United States Patent [19]

Valcavi

[11] Patent Number: 4,816,472
[45] Date of Patent: Mar. 28, 1989

[54] DERIVATIVES OF 19,20-BIS-NOR-PROSTANOIC ACID WITH ANTIULCER AND ANORECTIC ACTIVITY, PROCESS FOR THEIR PREPARATION AND PHARMACEUTICAL COMPOSITIONS THEREOF

[75] Inventor: Umberto Valcavi, Milan, Italy

[73] Assignee: Istituto Biochemico Italiano Giovanni Lorenzini S.p.A., Italy

[21] Appl. No.: 913,026

[22] Filed: Sep. 29, 1986

[30] Foreign Application Priority Data

Oct. 4, 1985 [IT] Italy ................................ 22358 A/85

[51] Int. Cl.$^4$ .................... C07C 177/00; A61K 31/557
[52] U.S. Cl. ...................................... 514/428; 514/530; 514/561; 514/563; 560/121; 562/503
[58] Field of Search ........................ 560/121; 562/503; 514/530, 563, 561, 428

[56] References Cited

U.S. PATENT DOCUMENTS

| | | |
|---|---|---|
| 4,018,811 | 4/1977 | Schaub et al. . |
| 4,073,938 | 2/1978 | Valcavi ................................ 424/317 |
| 4,074,056 | 2/1978 | Schaub et al. . |
| 4,547,521 | 10/1985 | Guzzi et al. .......................... 514/530 |

FOREIGN PATENT DOCUMENTS 2535343 2/1976 Fed. Rep. of Germany ...... 562/503

OTHER PUBLICATIONS

Otaf, Fifth Report pp. 74–75 Aug. 1975 US Dept. of Commerce.
"Protaglandins and the Arachidonic Acid Cascade" by Norman A. Nelson et al., C&EN, Aug. 16, 1982, pp. 30–44.
"Development and Therapeutic Role of Synthetic Prostaglandins in Peptic Ulcer Disease" by Paul W. Collins, Journal of Medicinal Chemistry, vol. 29, No. 4, Apr. 1986, pp. 437–443.

*Primary Examiner*—Robert Gerstl
*Attorney, Agent, or Firm*—Ostrolenk, Faber, Gerb & Soffen

[57] ABSTRACT

9-amino-19,20-bisnorprostanoic acids are useful for depressing appetite.

8 Claims, No Drawings

DERIVATIVES OF 19,20-BIS-NOR-PROSTANOIC ACID WITH ANTIULCER AND ANORECTIC ACTIVITY, PROCESS FOR THEIR PREPARATION AND PHARMACEUTICAL COMPOSITIONS THEREOF

DESCRIPTION OF THE INVENTION

The causes of peptic ulcer are not completely known. It does seem to be established, however, that there exists a balance between the factors which tend to promote ulceration, such as excessive secretion of acid or pepsin, and those which protect the mucosa, such as mucus secretion and the rate of formation of new membrane cells.

Among the numerous therapies indicated for the treatment of peptic ulcer, the natural prostaglandins and, successively, their analogues have been studied in this regard over the last decade.

Amongst the drugs belonging to this new class, and presently being processed for the market, are Misoprostol (BE 827.127, DE-OS 2.513.212 to G. D. Searle & Co. Ill.) and Rosaprostol (IT 1.060.366 issued July 10, 1982 to the Assignee hereof).

It was previously found that utilizing an 18 carbon atom skeleton and simplifying the structure of $PGE_1$, it was possible to obtain in particular a drug (Rosaprostol) which, although maintaining the antiulcer properties of the natural prostaglandins, completely loses the others.

Working on this new skeleton, it has now surprisingly been found that the substitution of an amino group for the oxygen at 9 position yields the derivatives with antiulcer activity dinstinctly superior to that of the parent compound Rosaprostol (viz. 9-hydroxy-9l,20-bis-nor-prostanoic acid sodium salt) from which they derive.

These new compounds correspond to the following formula (I)

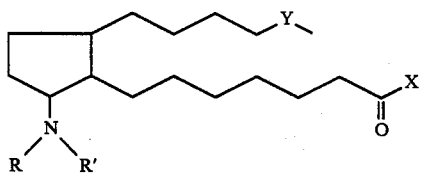

(I)

wherein:

R and R' can be the same or different and each represents H, a linear or branched alkyl, alkenyl, alkynyl, ($C_1$–$C_5$)-acyl group, —$CH_2COOH$, —$SO_2NH_2$, —$COCH(NH_2)CH_2SH$, or taken together, a 3 to 8-membered ring, the members of which may be a carbon atom or any one of the heteroatoms N, O, S.

X is hydroxy, a ($C_1$–$C_5$)-alkoxy, phenoxy benzyloxy or a —NHR'' group (wherein R'' is ($C_1$–$C_5$)-alkyl or H).

Y is —$CH_2$,

O, S, =NH, —$NCH_3$.

Compounds of the general formula (I) wherein Y=$CH_2$, R=H, and R'=H, ($C_1$–$C_4$)-alkyl are the subject matter of IT 1060366 (of the Assignee) in which their activity as hypolipaemics, inhibitors or platelet aggregation and hepatic protectors is disclosed. For that reason they are not claimed per se in the present patent, whereas their therapeutic use as appetite depressors and antiulcer agents is claimed herewith.

The invention includes also the pharmaceutically acceptable cationic salts of the compounds of formula (I), when X=OH, and in general all the pharmaceutically acceptable anionic salts.

The expression "pharmaceutically acceptable cationic salts", as used herein, refers to salts with alkali or alkaline earth metals such as, e.g. calcium, magnesium, sodium, potassium or salts of aluminum, ammonia, zinc and of organic amines such as, e.g. triethanolamine, and also amino acids, such as lysine, arginine, phenylalanine and proline, internal salts and salts of basic resins.

The expression "pharmaceutically acceptable anionic salts", as used herein, refers to salts obtained by the addition of an inorganic acid, such as, e.g. hydrochloric, hydrobromic, nitric, phosphoric, sulphuric, or by the addition of an organic acid such as, e.g. benzenesulphonic, benzoic, citric, laurylsulphonic, fumaric, oxalic, maleic, methanesulphonic, tartaric, ascorbic, p-toluenesulphonic, salicylic or succinic. With polybasic acids, the salt can be one having more than a mole of base per mole of acid. Nevertheless salts are formed of one mole of acid per one mole of product are preferred.

The anitulcer activity of these derivatives was evaluated on ulcers induced by the administration of ethanol, hydrochloric acid and sodium hydroxide in the rat, also on gastric ulcers induced by aspirin in the rat, and on their influence on gastric secretions in the rat.

The compounds can be prepared, e.g. according to the following reaction schemes:

(A) When R=R'=H and Y is defined as hereabove. Starting from the corresponding ketone, with hydroxylamine to obtain the oxime of formula (III)

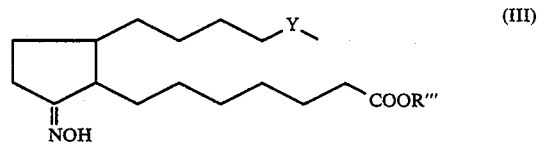

(III)

The oxime is then reduced with hydrogen to the desired amines.

(B) When R, R', X and Y have the meanings given for formula (I). Starting from the corresponding ketone, through a reductive amination with RR'NH. The carboxylic group is then transformed in the final ester-amide-acid and so on, according to per se known methods.

The starting ketone can be obtained in two different ways.

(C) When

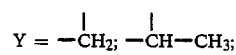

—O—. Starting from the cyclopentenone (VI) through an organo copper (II) reagent:

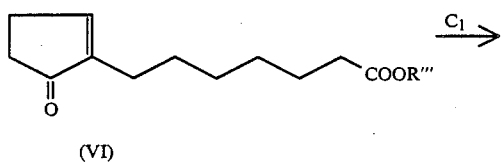

(VI)

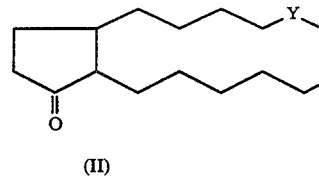

(II)

(D) When Y=NH, NCH₃S.
According to the following scheme:

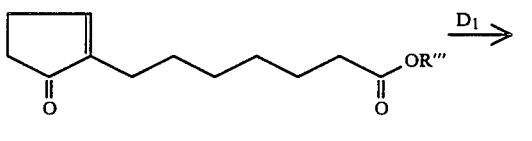

(VI)

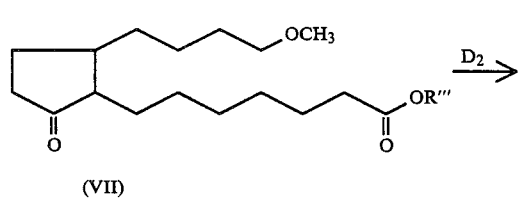

(VII)

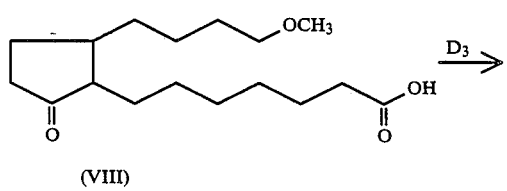

(VIII)

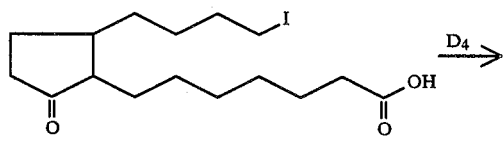

(IX)

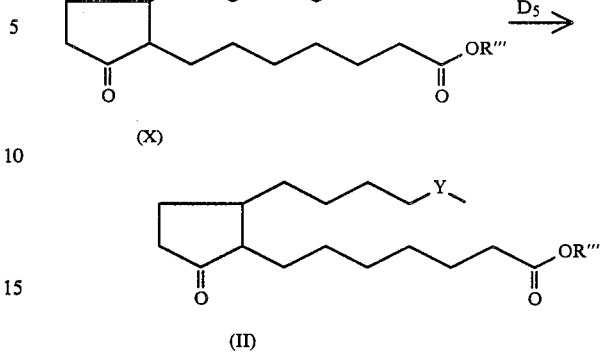

(X)

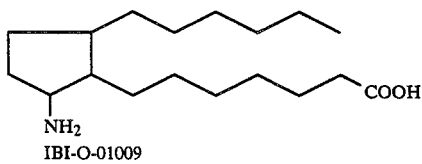

(II)

Reagents:

$D_1 = IMg\frown\frown OCH_3$,

CuI; $D_2$=KOH, MeOH; $D_3$=Me$_3$SiI; $D_4$=R'''OH, H⁺; $D_5$=CH$_3$Y⁻.

The pharmaceutically acceptable cationic salts of the compounds of the present invention are readily prepared by allowing the acidic form to react with the appropriate base, normally 1 equivalent, in a co-solvent. Suitable bases are, e.g. sodium hydroxide, sodium bicarbonate, sodium methoxide, sodium ethoxide, sodium hydride, potassium hydroxide, magnesium hydroxide, calcium hydroxide and so on.

Salts obtained by addition of acids are prepared by allowing the free base to react with the appropriate organic mineral acid (see above).

The examples and compounds given here below are only illustrative of the invention and shall not be construed restrictively. The activity of the inventive compounds as antiulcer agents was determined by the following series of tests.

(1) Ethanol induced ulcers in the rat:

The method used is that described by A. Robert et al, in Gastroenterology 77,433 (1979), the disclosure of which is incorporated herein by reference.

TABLE 1

Percent inhibition of ethanol induced ulcers in the rat.

| Compound Code | DOSE mg/kg | | | | | |
|---|---|---|---|---|---|---|
| | 100 | 50 | 25 | 10 | 5 | 2.5 |
| 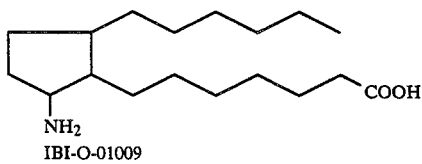 IBI-O-01009 | N.D. | 88% | 67% | 70% | 50% | 40% |

TABLE 1-continued

Percent inhibition of ethanol induced ulcers in the rat.

| Compound Code | DOSE mg/kg | | | | | |
|---|---|---|---|---|---|---|
| | 100 | 50 | 25 | 10 | 5 | 2.5 |
| IBI-P-01013 (NHCH₃, COONa) | 91% | 91% | 86% | 67% | 44% | N.D. |
| IBI-P-01014 (N(CH₃)₂, COONa) | 91% | 97% | N.D. | 62% | 43% | 24% |
| IBI-P-01015 (NH-iPr, COONa) | N.D. | 65% | 34% | 9% | N.D. | N.D. |
| IBI-P-01012 (NHCOCH₃, COONa) | 78% | N.D. | N.D. | 25% | N.D. | N.D. |
| Rosaprostol (OH, COONa) | 37% | 9% | N.D. | N.D. | N.D. | N.D. |

N.D. Not determined.

(2) Hydrochloric acid induced ulcers in the rat:

The method used for this test is that described by A. Robert et al, in Gastroenterology, 77,433, (1979), the disclosure of which is incorporated herein by reference.

TABLE 2

Percent inhibition of HCl induced ulcers in the rat.

| Compound Code | DOSE mg/kg | | | |
|---|---|---|---|---|
| | 200 | 100 | 50 | 25 |
| IBI-O-01009 (NH₂, COOH) | 91% | 89% | 68% | N.D. |
| IBI-P-01013 (NHCH₃, COONa) | N.D. | 66% | 49% | 40% |
| IBI-P-01014 (N(CH₃)₂, COONa) | N.D. | 63% | 55% | 23% |
| IBI-P-01015 (NH-iPr, COONa) | N.D. | 54% | 46% | 0% |
| IBI-P-01012 (NHCOCH₃, COONa) | N.D. | N.D. | 66% | 15% |

TABLE 2-continued

Percent inhibition of HCl induced ulcers in the rat.

| Compound Code | DOSE mg/kg | | | |
|---|---|---|---|---|
| | 200 | 100 | 50 | 25 |
| 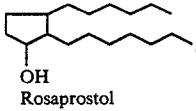
OH
Rosaprostol | 63% | 45% | N.D. | 15% |

N.D. = Not determined (3) Sodium hydroxide induced ulcers in the rat:

Also this test is performed in accordance with the method described by A. Robert et al, in Gastroenterology, 77,433 (1979), the disclosure of which is incorporated herein by reference.

For carrying out this test, the method described by H. A. Carmichael, L. M. Nelson, R. I. Russel in Gastroenterology 74, 1229 (1978) is used, the disclosure of which is incorporated herein by reference.

TABLE 4

Percent inhibition of aspirin-induced ulcers in the rat.

| Compound Code | % inhibition at a dose of 200 mg/kg of drug |
|---|---|
| 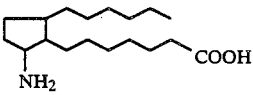
IBI-O-01009 | 72% |

TABLE 3

Percent inhibition of NaOH induced ulcers in the rat.

| Compound Code | DOSE mg/kg | | | | | | |
|---|---|---|---|---|---|---|---|
| | 200 | 100 | 50 | 25 | 12.5 | 10 | 5 |
| NH₂
IBI-O-01009 | N.D. | N.D. | N.D. | 80% | N.D. | 54% | 37% |
| NHCH₃
IBI-P-01013 | N.D. | N.D. | N.D. | 87% | 81% | N.D. | N.D. |
| N(CH₃)₂
IBI-P-01014 | N.D. | N.D. | 74% | 63% | 52% | N.D. | N.D. |
| NH-iPr
IBI-P-01015 | N.D. | N.D. | 54% | 46% | 13% | N.D. | N.D. |
| NHCOCH₃
IBI-P-01012 | N.D. | N.D. | 59% | 19% | 7% | N.D. | N.D. |
| OH
Rosaprostol | 92% | 84% | 53% | // | // | // | // |

N.D. Not determined (4) Aspirin induced gastric ulcers in the rat:

TABLE 4-continued

Percent inhibition of aspirin-induced ulcers in the rat.

| Compound Code | % inhibition at a dose of 200 mg/kg of drug |
|---|---|
| 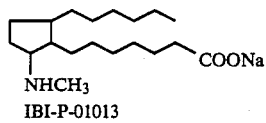 IBI-P-01013 | 87% |
| 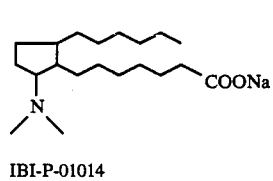 IBI-P-01014 | 88% |
| 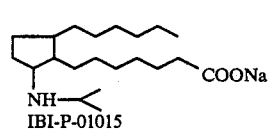 IBI-P-01015 | 63% |
| 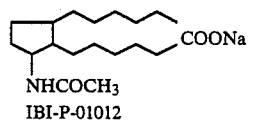 IBI-P-01012 | 58% |
| 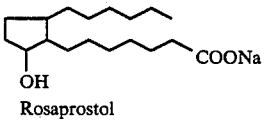 Rosaprostol | 64% |

(5) Gastric secretion in the rat:

Sprague-Dawley rats of both sexes are used for this test. The gastric secretion is rated according to the method described by H. Shay et al in Gastroenterology 5,43 (1945) the disclosure of which is incorporated herein by reference.

TABLE 5

Percent inhibition of gastric secretion in the rat 2 and 4 hours after treatment

| Compound Code | DOSE mg/kg | | | | | | | |
|---|---|---|---|---|---|---|---|---|
| | 100 | | 50 | | 25 | | 12.5 | |
| | 2h | 4h | 2h | 4h | 2h | 4h | 2h | 4h |
| 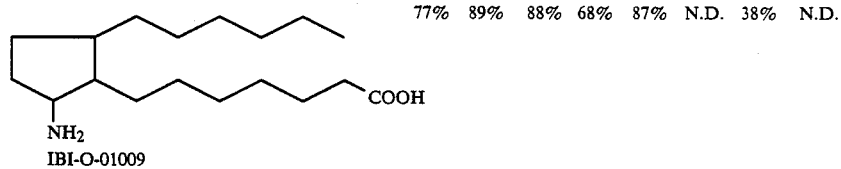 IBI-O-01009 | 77% | 89% | 88% | 68% | 87% | N.D. | 38% | N.D. |
| 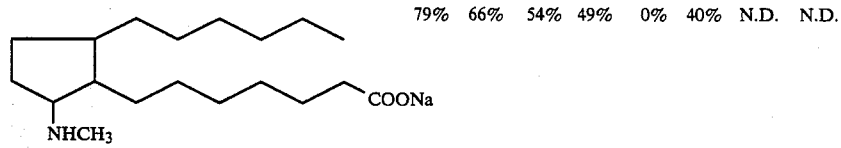 IBI-P-01013 | 79% | 66% | 54% | 49% | 0% | 40% | N.D. | N.D. |
| 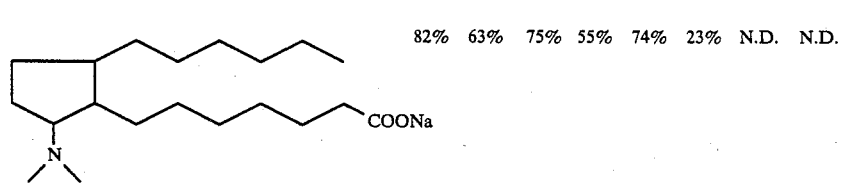 IBI-P-01014 | 82% | 63% | 75% | 55% | 74% | 23% | N.D. | N.D. |
| 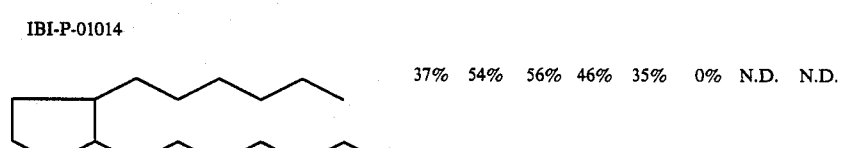 IBI-P-01015 | 37% | 54% | 56% | 46% | 35% | 0% | N.D. | N.D. |
| 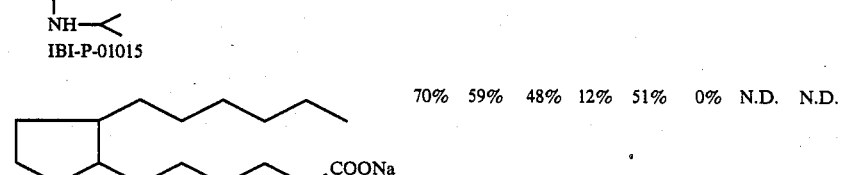 IBI-P-01012 | 70% | 59% | 48% | 12% | 51% | 0% | N.D. | N.D. |

TABLE 5-continued

Percent inhibition of gastric secretion in the rat
2 and 4 hours after treatment

| | DOSE mg/kg | | | | | | | |
|---|---|---|---|---|---|---|---|---|
| | 100 | | 50 | | 25 | | 12.5 | |
| Compound Code | 2h | 4h | 2h | 4h | 2h | 4h | 2h | 4h |
| [cyclopentane with OH and long chain COONa] Rosaprostol | 50% | 45% | 30% | N.D. | 0% | 15% | N.D. | N.D. |

N.D. Not determined.

The activity of the compounds of the instant invention in the here reported tests unfolds on two different levels: on the one hand there is a cytoprotection of the gastric mucosa against lesion-causing agents, such as ethanol, which act directly, or such as aspirin, which act indirectly. On the other hand, there is partial inhibition of acid secretion which thus favours the cicatrizing process of the mucosa. Such activity reflects the utility of these drugs in the treatment of peptic ulcers in mammals including man.

These compounds should preferably be administered as a pharmaceutical composition in admixture with one or more pharmaceutically acceptable diluents and/or excipients. They are preferably administered orally (for example as tablets, granules, syrups, etc.) or parenterally (i.v. or i.m.). Although the dose required will vary according to the symptoms, sex, weight and condition of the patient, and also according to the frequency and route of administration, for the purpose of this patent the compounds according to the present invention can be administered to an adult in a daily dosage of from 0.1 to 1500 mg, preferably of from 1 to 1000 mg, in a single dosage or in subdivided dosages over a period of 24 hours.

The excipients for the pharmaceutical compositions for oral administration are those usually employed by the pharmaceutical industry for making tablets, granules or syrups, such as, e.g. starch, lactose, Aerosil[(1)], magnesium stearate, talc, glycine, sodium carbonate, polyethylene glycol, glucose, saccharose, carboxymethylcellulose, natural flavourings, polysorbates, pharmacoat, and so on.

Moreover, the compounds of the instant invention can be employed as anorectics. It has in fact been found and it is claimed herein that the subject compounds, at appropriate dosages, slow down the rate of gastric depletion, thus depressing the appetite, not by an effect on the central nervous system, as is normally the case with other known anorectics, but via a mechanism which, although not completely clear, appears to be more natural and completely new.

This second pharmaceutical activity is assessed through the following test.

Gastric depletion in the rat.

Rats of both sexes and mean weight of 180–200 g are used. The animals are subjected to fasting for 24 hours but have free access to water up to 3 hours prior to the test.

Experimental scheme:
time O: drug or solvent
time +30′: phenyl red
time +50′: sacrifice.

(1) Aerosil is a brand of colloidal silicon dioxide, made by Degussa, U.K.

Preparation of phenyl red solution: 50 mg of phenyl red is mixed with 100 ml of a 1.5% methyl cellulose solution and shaken for 5 hours.

1.5 ml per rat is administered irrespective of weight.
Methodology:

The rats are sacrificed by cervix translocation: the stomach is taken out after ligaturing the cardias and pilorus.

The entire stomach and contents are placed in the container of a homogenizer with 50 ml of 0.1N NaOH. They are homogenized for 2 minutes at a maximum velocity. They homogenate is transferred to a test-tube and left to settle for one hour.

5 ml of the supernatant is taken out and put into a centrifuge tube and mixed with 0.5 ml of 20% (w/v) trichloroacetic acid. The tube is centrifuged at 2500 rpm for 20 min. The entire supernatant is taken and mixed with 4 ml of 0.4N NaOH, and its absorbance is measured at 560λ.

Gastric depletion is calculated according to the following formula:

$$(1 - \text{sample absorbance}/\text{standard absorbance}) \times 100$$

As "standard absorbance" is considered the mean value of spectophotometric measurement of 4 animals sacrificed immediately after administering phenyl red.

Table 6 summarizes the inhibition values of gastric depletion.

TABLE 6

| | DOSE mg/kg | | |
|---|---|---|---|
| Compound Code | 100 | 50 | 25 |
| [cyclopentane with NH2 and chain COOH] IBI-O-01009 | 80% | 80% | 18% |
| [cyclopentane with NHCH3 and chain COONa] IBI-P-01013 | N.D. | 33% | N.D. |
| [cyclopentane with N and chain COONa] IBI-P-01014 | N.D. | 55% | N.D. |

TABLE 6-continued

| Compound Code | DOSE mg/kg | | |
|---|---|---|---|
| | 100 | 50 | 25 |
| 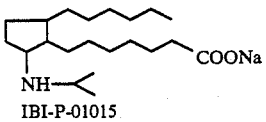 IBI-P-01015 | N.D. | 14% | N.D. |
| 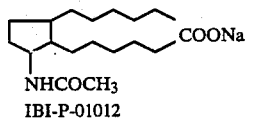 IBI-P-01012 | N.D. | 78% | N.D. |

N.D. Not determined.

EXAMPLE 1

9-hydroxyimino-19,20-bis-nor-prostanoic acid of formula (III) wherein R'''=H and Y=—CH$_2$.

A solution of 9-keto-19,20-bis-nor-prostanoic acid of formula (II) wherein R'''=H and Y=CH$_2$, (196.5 g) in methanol (2.3 l) at room temperature, is mixed, over 20 min., with a solution of sodium acetate (300 g) and hydroxylamine hydrochloride (240 g) dissolved in water (2.3 l) and in methanol (2.3 l). The reaction mixture is kept 4 hours at room temperature under stirring. The methanol is evaporated at 50° C. using a pulsor, the residue is taken up with methylene chloride (2 l) and separated.

The aqueous phase is extracted with more methylene chloride (500 ml). The combined organic phases are washed with water (1 l), dried and evaporated yielding a crude product (200.5 g) which is crystallized from pentane (B 400 ml) and ethyl ether (200 ml).

The crystallized product (110 g) has a m.p. of 51°–52° C.

EXAMPLE 2

9-amino-19,20-bis-nor-prostanoic acid of formula (I) wherein R=R'=H, Y=—CH$_2$, X=OH (Compound IBI-P-01009).

A solution of the oxime (200 g) obtained in Example 1, in methanol (2 l), is mixed with platinum oxide (10 g).

The thus prepared mixture is put in a glass vessel under hydrogen (hydrogen pressure approx. 1 atm.) and stirred; then the reaction mixture is filtered and the solvent is evaporated.

The crude product (202.5 g) is washed with ethyl ether (4 l), suspended in acetone (250 ml), and filtered, yielding the pure title compound (82.5 g), m.p. 159°–160° C.

| Elemental analysis | Calculated | Found |
|---|---|---|
| C | 72.67% | 72.81% |
| H | 11.86% | 11.72% |
| N | 4.71% | 4.75% |

EXAMPLE 3

Sodium salt of 9-methylamino-19,20-bis-nor-prostanoic acid of formula (I) wherein R=H, R'=C$_3$, Y=CH$_2$, X=ONa (Compound IBI-P-01013).

A solution of the methyl ester of 9-keto-19,20-bis-nor-prostanoic acid of formula (II), wherein R'''=Me and Y=CH$_2$, (31 g) dissolved in ethanol (20 ml), is mixed with 2.5% solution of methylamine in ethanol (10 ml) and platinum oxide (0.1 g).

The mixture is stirred overnight at 50° C. under hydrogen (pressure: 2 amt).

The reaction mixture is then cooled to ambient temperature, filtered off and evaporated under reduced pressure. The oily residue is taken up with 0.5M HCl (500 ml) and extracted with hexane (2×200 ml).

The organic phase is combined, dried and dessicated. The unmodified starting material is recovered (13.2 g). The acid aqueous phase is adjusted to pH 8 with bicarbonate, extracted with methylene chloride (3×200 ml). The combined organic phases are dried and evaporated under reduced pressure.

The residue is suspended in a solution of 1M NaOH (100 ml), heated to 70° C. and stirred until a clear solution results (2–3 hours). The solution is cooled to ambient temperature, acidified to pH=5 and then extracted with methylene chloride (2×100 ml). The combined, dried organic phases are evaporated. The residue is taken up with tetrahydrofuran (40 ml), treated with 2 equivalents of a 1 molar solution of NaHCO$_3$ and dessicated. The dessicated mixture is taken up with methylene chloride (200 ml), filtered off and dessicated to yield the desired product (15.7 g).

Analysis (performed on the free acid): IR($v$max, cm$^{-1}$): 2920, 2860, 1710 $^1$H-NMR(CDCl$_3$) δ: 9.5 (s, 1H); 2.9 (m, 1H); 2.4 (s, 3H), 2.2 (t, 2H); 1.3 (broad s, 26H); 0.9 (t, 3H).

EXAMPLE 4

Sodium salt of 9-dimethylamino-19,20-bis-nor-prostanoic acid of formula (I) wherein R=R'=CH$_3$, Y=CH$_2$, X=ONa. (Compound IBI-P-01014).

One proceeds as in Example 3, using the same starting methyl ester and dimethylamine in ethanol (14.3 ml of a 5.6 molar solution) to yield after work-up the title product (11.3 g).

Analysis (formed on the free acid): IR ($v$max, cm$^{-1}$): 2940 2860, 1710, $^1$H—NMR: 10.8 (s, 1H); 2.4 (2s, 6H); 2.2 (t, 2H); 1.3 (broad s, 26H); 0.9 (t, 3H).

EXAMPLE 5

Sodium salt of 9-isopropylamino-19,20-bis-nor-prostanoic acid of formula (I) wherein R=H, R'=—CH(CH$_3$)$_2$, Y=CH$_2$, X=ONa. (Compound IBI-P-01015).

One proceeds as in Example 3, using the same starting methyl ester (31 g) and isopropylamine (4.7 g) in ethanol (30 ml) to yield after work-up the title product (12.5 g).

Analysis (performed on the free acid): IR ($v$max, cm$^{-1}$): 2940, 2860, 1710, $^1$H—NMR(CDCl$_3$): 8.8 (s, 1H); 3.2 (m, 2H); 2.2 (m, 2H); 1.3 (m, 32H); 0.9 (t, 3H).

EXAMPLE 6

Methyl ester of 9-keto-17-oxa-prostanoic acid of formula (II) wherein R''=Me and Y=O.

A magnesium (13 g) suspension in tetrahydrofuran (390 ml) containing a catalytic quantity of iodine (approx. 0.1 g) is mixed with (4-bromo-n-butyl)-methyl ether (9 g). It is heated to reflux, and further (4-bromo-n-butyl)-methyl ether (81.2 g) is added dropwise, under heating, over 25 minutes.

The reaction mixture is refluxed for 10 minutes, cooled to 20° C. and diluted with THF (390 ml); then cooled further to 5° C., mixed with cuprous iodide (5.1 g) and kept 1 hour at 0°–5° C. The mixture is then cooled to −35° C. and 7-(5-ketocycopentenyl)-heptanoic acid methyl ester (VI, R″=Me) is added dropwise thereto.

The temperature is allowed to rise spontaneously for 10 minutes. The mixture is poured into water (500 ml). The organic phase is separated, dried and evaporated under reduced pressure, yielding a crude product (84.8 g) which is chromatographed on a silica column to yield the pure title product (64.9 g).

| Elemental analysis | Calculated | Found |
|---|---|---|
| C | 69.18% | 69.22% |
| H | 10.32% | 10.23% |

EXAMPLE 7

9-keto-17-oxa-prostanoic acid of formula (II) wherein R″=H and Y=O.

A methanol (2 ml) solution of NaOH (128.2 mg) is mixed with the ester obtained in Example 6 dissolved in methanol (1 ml), at ambient temperature, over a period of 5 minutes. The thus obtained solution is left to reflux for 3 hours, cooled, mixed with water (10 ml) and 1N HCl to pH 1. The reaction mixture is extracted with ether (3×100 ml). The ether phase is washed with brine (3×10 ml), then brought to pH 3 with 1N HCl.

The organic phase is separated, dried, evaporated under reduced pressure, yielding a crude product (0.41 g) which, after silica chromatography, yields the title acid (0.4 g).

| Elemental analysis | Calculated | Found |
|---|---|---|
| C | 68.42% | 68.63% |
| H | 10.13% | 10.18% |

EXAMPLE 8

Sodium salt of N-acetyl-9-amino-19,20-bis-nor-prostanoic acid of formula (I), wherein R=H, R′=CH$_3$CO, Y=CH$_2$, X=ONa (IBI-P-01012)

A solution of the title compound (25 g) of Example 2 (IBI-01009) in DMF (260 ml) is prepared and mixed, at 0° C., with triethylamine (25.4 g). After 5 minutes stirring, acetyl chloride (9.9 g) is added dropwise. The reaction mixture is left under stirring for 10 minutes, poured into water, and after acidifying with diluted hydrochloric acid, it is extracted with ethyl ether (4×400 ml). The thus extracted crude material is purified by silica gel chromatography using diethyl acetate as the eluent. The so-obtained acid (21 g) is dissolved in a NaOH (2.5 g) solution in methanol (37.5 ml). This solution is then concentrated to half its volume at room temperature whereupon it is mixed with acetonitrile (500 ml). The thus obtained precipitate (18 g) is filtered off.

| Elemental analysis | Calculated | Found |
|---|---|---|
| C | 66.3% | 66.5% |
| H | 9.9% | 9.8% |
| N | 4.14% | 4.3% |

I claim:

1. A method of depressing appetite in a host in need thereof comprising administering to said host an appetite depressing effective amount of a compound of general formula (I)

wherein R and R′ can be the same or different and each represents a straight or branched alkyl, alkenyl, alkynyl, (C$_1$-C$_5$)-acyl group, —CH$_2$COOH, —SO$_2$NH$_2$, —COCH(NH$_2$)CH$_2$SH, or when taken together, they can form a 3 to 8-membered ring, the members of which can be a carbon atom or a heteroatom, X is a hydroxy, (C$_2$-C$_5$)-alkoxy, phenoxy, benzyloxy group or NHR″ (wherein R″ is a (C$_1$-C$_5$)-alkyl group or H), Y is =CH$_2$, ≡CHCH$_3$, O, S, =NH, or —NCH$_3$.

2. A method of depressing appetite according to claim 1 wherein said compound is where
X is OH or ONa
R is H or CH$_3$
and R′ is H, CH$_3$, isopropyl or COCH$_3$.

3. A method of depressing appetite according to claim 1 wherein X is OH.

4. A method of depressing appetite according to claim 3 wherein Y is =CH$_2$.

5. A method of depressing appetite according to claim 4 wherein R and R′ taken together are —CH$_2$—CH$_2$—CH$_2$—CH$_2$— forming a pyrrolidine heterocycle with the nitrogen atom.

6. A method of depressing appetite according to claim 3 where Y is —CH(CH$_3$)—.

7. A method of depressing appetite according to claim 3 where Y is S.

8. A method of depressing appetite according to claim 3 where Y is O.

* * * * *